United States Patent [19]

Sano et al.

[11] Patent Number: 4,476,008

[45] Date of Patent: Oct. 9, 1984

[54] OXYGEN CONCENTRATION-SENSING DEVICE AND THE METHOD OF PRODUCING THE SAME

[75] Inventors: Hiromi Sano, Nagoya; Masatoshi Suzuki, Anjo; Masaya Fujimoto, Oobu; Masahiro Shibata, Aichi; Toshitaka Saito, Toyohashi; Mitihiro Yamakawa, Kariya, all of Japan

[73] Assignee: Nippondenso Co., Ltd., Japan

[21] Appl. No.: 541,001

[22] Filed: Oct. 11, 1983

[30] Foreign Application Priority Data

Oct. 12, 1982 [JP] Japan .................................. 57-178643

[51] Int. Cl.$^3$ ........................ G01N 27/58; B05D 1/12
[52] U.S. Cl. .................................. 204/425; 204/429; 427/34; 427/126.4
[58] Field of Search ........................ 204/429, 425, 15; 427/34, 126.4

[56] References Cited

U.S. PATENT DOCUMENTS

| | | | |
|---|---|---|---|
| 4,097,353 | 6/1978 | Kishida et al. | 204/429 X |
| 4,164,462 | 8/1979 | Ichikawa et al. | 204/429 |
| 4,265,930 | 5/1981 | Shinohara et al. | 427/34 |
| 4,356,065 | 10/1982 | Dietz | 204/1 T |
| 4,359,374 | 11/1982 | Sano et al. | 204/429 |
| 4,402,820 | 9/1983 | Sano et al. | 204/429 X |

Primary Examiner—G. L. Kaplan
Attorney, Agent, or Firm—Cushman, Darby & Cushman

[57] ABSTRACT

An oxygen gas concentration-sensing device comprises a solid electrolyte body which is prepared from an oxygen ion-permeable metal oxide and whose first surface is exposed to the gas to be sensed and the second surface is exposed to a reference gas. First and second electrodes are respectively pressed against the first and second surface of the solid electrolyte body. The first electrode exposed to the gas is covered with a porous gas diffusion-resisting layer. This gas diffusion-resisting layer is chosen to have an average pore-size ranging from 300 Å to 400 Å.

14 Claims, 6 Drawing Figures

OXYGEN CONCENTRATION-SENSING DEVICE AND THE METHOD OF PRODUCING THE SAME

BACKGROUND OF THE INVENTION

This invention relates to an oxygen concentration-sensing device and the method of producing the same, and more particularly to an oxygen concentration-sensing device for sensing the oxygen concentration in the exhaust of an internal combustion engine.

To cope with the exhaust of an internal combustion engine, oxygen concentration-sensing devices are widely known. This device is applied to determine the air-fuel ratio of a gas mixture taken into the combustion chamber of an internal combustion engine from the level of oxygen concentration in the exhaust. When, therefore, the air-fuel ratio of a gas mixture is so controlled by said device as to conform to a theoretical air-fuel ratio, it is possible to reduce the amount of harmful gas components such as CO, HC, NOx contained in the exhaust. Further, such a device can control the air-fuel ratio of the gas mixture to be greater than the theoretical air-fuel ratio, thereby decreasing fuel consumption.

Description will now be given of the fundamental construction of the above-mentioned oxygen concentration-sensing device. This device which is formed of an oxygen-ion-permeable metal oxide comprises a solid electrolyte body having a first surface exposed to a gas to be sensed and a second surface exposed to a reference gas, a first electrode fixed to the first surface of the solid electrolyte body, a second electrode fixed to the second surface of the solid electrolyte body, and a gas diffusion-resistant layer coated on the first electrode.

Description will now be given of the operation of the oxygen concentration-sensing device constructed as described above. When a voltage is impressed between the first and second electrodes, oxygen ions of an amount corresponding to the oxygen concentration in the exhaust diffuse through the solid electrolyte body, causing a current corresponding to the oxygen concentration in the exhaust to flow across both electrodes. When a higher voltage than prescribed is impressed across both electrodes, the current flowing through both electrodes remains substantially constant regardless of the magnitude of the voltage. The substantially constant current is referred to as a saturated current. Therefore, measurement of this saturated current indicates the oxygen concentration in the exhaust.

It is known that the value $Il$ of the saturated current can be determined from the following formula:

$$Il \simeq \frac{4F \cdot DO_2}{R \cdot T} \cdot \frac{E}{l} \cdot S \cdot PO_2$$

where:
F = Faraday constant
R = gas constant
$DO_2$ = diffusion constant of oxygen molecule
T = absolute temperature of a solid electrolyte body
E = rate of gas (oxygen molecule) diffusion through a gas diffusion-resistant layer
l = effective gas diffusion distance in the gas diffusion-resisting layer
S = electrode area
$PO_2$ = partial pressure of oxygen molecule As seen from the above formula, the value $Il$ of the saturated current varies due to different factors. If, therefore, it is attempted to exactly determine the value $Il$ of the saturated current corresponding to the oxygen concentration in the exhaust, it is necessary to accurately define the different factors. Attention must be paid particularly to the extent to which the saturated current $Il$ is affected by the various factors except for the above-mentioned constants, namely, the absolute temperature T and the gas diffusion rate E in the gas diffusion-resistant layer.

In this connection, reference is made to the U.S. Pat. No. 4,356,065 which sets forth the effect of the diffusion rate E in the gas diffusion-resistant layer on the value $Il$ of the saturated current and the process of eliminating said effect. However, U.S. Pat. No. 4,356,065 pays attention only to the diffusion rate E in the gas diffusion-resistant layer, and pays no heed to the absolute temperature T indicated in the aforementioned formula.

The present inventors investigated the effects of absolute temperature T on the value $Il$ of the saturated current. As a result, it has been disclosed that the relationship shown in FIG. 1 exists between the value $Il$ of the saturated current and the absolute temperature T. It is obvious that the value $Il$ of the saturated current varies with the absolute temperature T. For the precise determination of the value $Il$ of the saturated current, therefore, it is necessary to maintain the temperature of the solid electrolyte body at a substantially constant level. However, considerable difficulties are encountered in setting the temperature of the solid electrolyte body at a constant level by means of, for example, a heater element. If it is tried to preserve the constant temperature of the solid electrolyte body by means of the heater element, then the resultant device will have a very complicated arrangement.

SUMMARY OF THE INVENTION

It is, accordingly, the object of this invention to provide an oxygen concentration-sensing device which greatly reduces the extent to which the value $Il$ of the saturated current is affected by the temperature, thereby practically eliminating the necessity of making any compensation for the temperature of a solid electrolyte body. To attain the above-mentioned object, this invention provides an oxygen concentration-sensing device which comprises a solid electrolyte body which is formed of an oxygen ion-permeable metal oxide and whose first surface is exposed to a gas to be sensed and whose second surface is exposed to a reference gas, a first porous electrode fixed to the first surface of the solid electrolyte body, a second porous electrode fixed to the second surface of the solid electrolyte body, a gas diffusion-resisting layer prepared from a porous metal oxide having an average pore-size of 300 to 400 Å and coated on the first electrode, and means for impressing a prescribed voltage across the first and second electrodes.

DETAILED DESCRIPTION OF THE PREFERRED EMBODIMENTS

Figure 1:
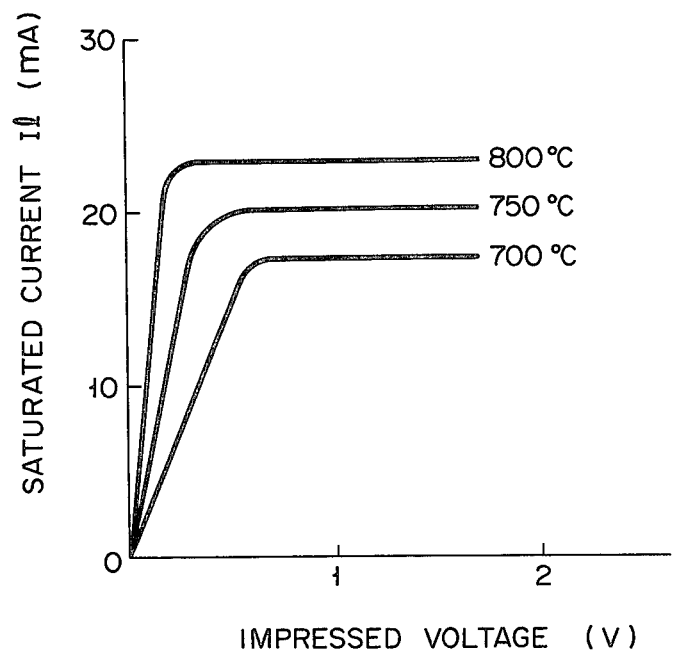
FIG. 1 is a curve diagram showing the dependency of the value $Il$ of the saturated current on temperature.
Figure 2:
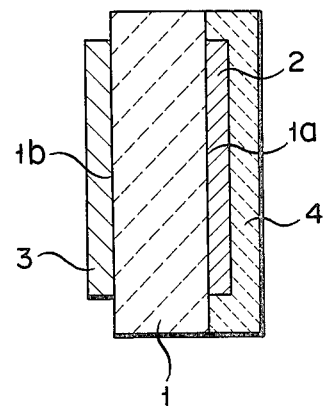
FIG. 2 is a typical cross-sectional view of the fundamental structure of the main part of an oxygen concentration-sensing device embodying this invention.

FIG. 2 shows the fundamental structure of the main part of an oxygen concentration-sensing device embodying this invention. The device comprises an oxygen ion-permeable solid electrolyte body 1. A first surface 1a of the body 1 is exposed to a gas to be sensed, namely, the exhaust from an internal combustion engine. A first porous electrode 2 is fixed to the first surface 1a. A second surface 1b of the body 1 is exposed to a reference gas, namely, the atmosphere. A second porous electrode 3 is fixed to the second surface 1b. The first electrode 2 is covered with a porous gas diffusion-resisting layer 4.

Description will now be given of the function of the subject oxygen concentration-sensing device having the above-mentioned fundamental structure. When voltage is impressed across the first electrode 2 and second electrode 3, oxygen molecules contained in an exhaust conducted through the gas diffusion-resisting layer 4 to the first electrode 2 are converted into oxygen ions when receipt of electrons from the first electrode 2. The oxygen ions diffuse through the body 1 and are brought to the second electrode 3, where the oxygen ions release electrons and are returned to oxygen molecules. Namely, current flows across the first electrode 2 and second electrode 3.

When higher voltage than prescribed is impressed across the first electrode 2 and second electrode 3, then the aforementioned saturated current, whose level remains unchanged, flows across said electrodes 2, 3, no matter how the voltage level is changed. As seen from the aforesaid formula, the value Il of the saturated current varies with an oxygen concentration (oxygen partial pressure) in the exhaust. Therefore, measurement of the value Il indicates the oxygen concentration in the exhaust.

As previously described, the value Il of the saturated current indeed varies with the temperature of the solid electrolyte body 1. The present inventors studied the relationship of the temperature dependency of the value Il of the saturated current and the diffusion rate of oxygen gas through the gas diffusion-resisting layer 4, that is, the average pore-size of said gas diffusion-resisting layer 4. As a result, the relationship shown in FIG. 3 was obtained. The solid electrolyte body 1 was chosen to have a standard temperature of 750° C. This temperature was varied at the rate of 50° C. between 850° and 650° C. The ordinate of FIG. 3 indicates the extent to which the value Il of the saturated current varies, each time temperature rises above or falls from the standard temperature of 750° C. at the rate of 50° C. The abscissa shows the average pore-size of the gas diffusion-resisting layer 4. It is seen from FIG. 3 that when the pore-size of the gas diffusion-resisting layer 4 decreases from 300 Å, the value Il of the saturated current presents a negative temperature dependency, whereas, when the average pore-size of the gas diffusion-resisting layer 4 increases above 300 Å, the value Il of the saturated current shows a positive temperature dependency.

Figure 3:
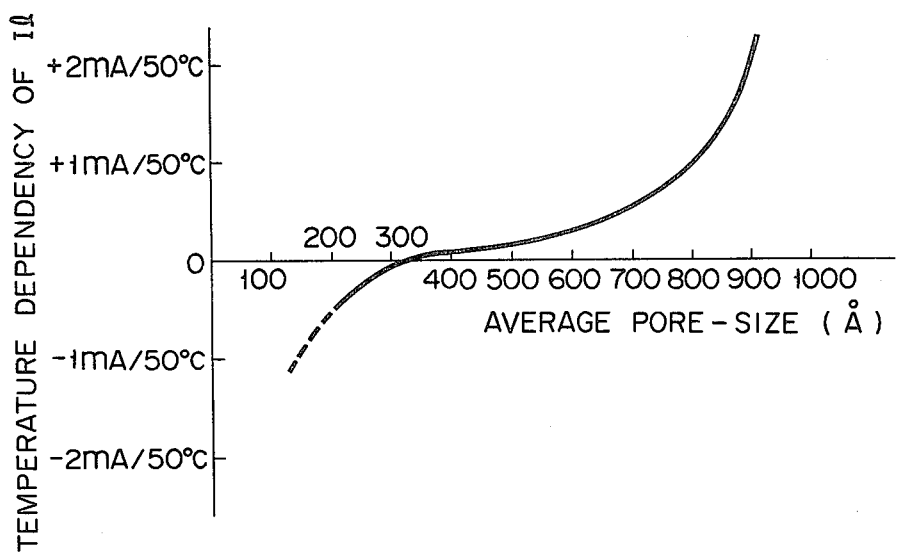
FIG. 3 is a curve diagram indicating the temperature dependency of the value $Il$ of the saturated current values to the average pore-size formed in the gas diffusion-resisting layer.

FIG. 3 further proves that while the average pore-size of the gas diffusion-resisting layer 4 remains within the range of 300 and 400 Å, the temperature dependency of the saturated current Il is extremely reduced. In other words, it is seen that while the solid electrolyte body 1 is operated at a temperature ranging between 850° and 650° C., the temperature dependency of the value Il of the saturated current is negligible.

The above-mentioned temperature range of 850° to 650° C. is substantially equal to a temperature level prevailing in the internal combustion engine. When, therefore, the device is applied in sensing the concentration of oxygen contained in the exhaust, it is practically unnecessary to make any temperature compensation for the value Il of the saturated current.

As already described, when the gas diffusion-resisting layer 4 is chosen to have an average pore-size ranging from 300 to 400 Å, the variation of the value Il of the saturated current with the temperature of the solid electrolyte body 1 can be extremely reduced. Therefore, the saturated current corresponding to the concentration of oxygen in the exhaust can be sensed with high precision without making any compensation for the temperature of the solid electrolyte body 1.

Description will now be given of the process of forming the gas diffusion-resisting layer (4). A uniform mixture consisting of 99 to 96% by weight of the powder (whose particle size ranges between 5 and 44 microns) of $MgO \cdot Al_2O_3$ (spinel) and 1 to 4% by weight of the powder (whose particle size ranges between 5 and 20 microns) of $SiO_2$ was plasma sprayed to the first surface 1a of the solid electrolyte body 1, thereby prefabricating the gas diffusion-resisting layer (4) over the first electrode 1a. The plasma spraying was carried out under the following conditions:

Gas composition = Ar and $N_2$
Flow rate of Ar = 20 l/min
Flow rate of $N_2$ = 10 l/min
Spraying current = 650 Å
Spraying voltage = 58 V
Spraying distance = 80 mm A gas diffusion-resisting layer 4 prefabricated under the above-mentioned condition of plasma spraying had a thickness of 50 to 200 microns and an average pore-size of 600 to 700 Å. The prefabricated gas diffusion-resisting layer 4 was baked for sintering for about 2 hours at a temperature of 1,300° C. to 1,400° C. The sintered layer 4 was formed of contiguous pores whose average pore-size ranged between 300 to 400 Å. This pore-size could be measured by a known mercury porosimeter.

The content of $SiO_2$, one of the components of the gas diffusion-resisting layer (4) and the average pore-size corresponding to the temperature at which said layer (4) was baked had the relationship shown in the following table.

| Amount of $SiO_2$ (% by weight) | 0 | 1 | 2 | 3 | 4 | 5 |
|---|---|---|---|---|---|---|
| Average pore-size of a gas diffusion-resisting layer baked at a temperature | 600 Å | 380 Å | 370 Å | 330 Å | 300 Å | 250 Å |

| Amount of SiO₂ (% by weight) | 0 | 1 | 2 | 3 | 4 | 5 |
|---|---|---|---|---|---|---|
| of 1,300° C. | | | | | | |
| 1,400° C. | | | | | | |

To enable the gas diffusion-resisting layer 4 to have an average pore-size of 300 to 400 Å, it is preferred, as seen from the above table, that the SiO₂ content of the gas diffusion-resisting layer 4 be set at 1 to 4%.

Figure 4:
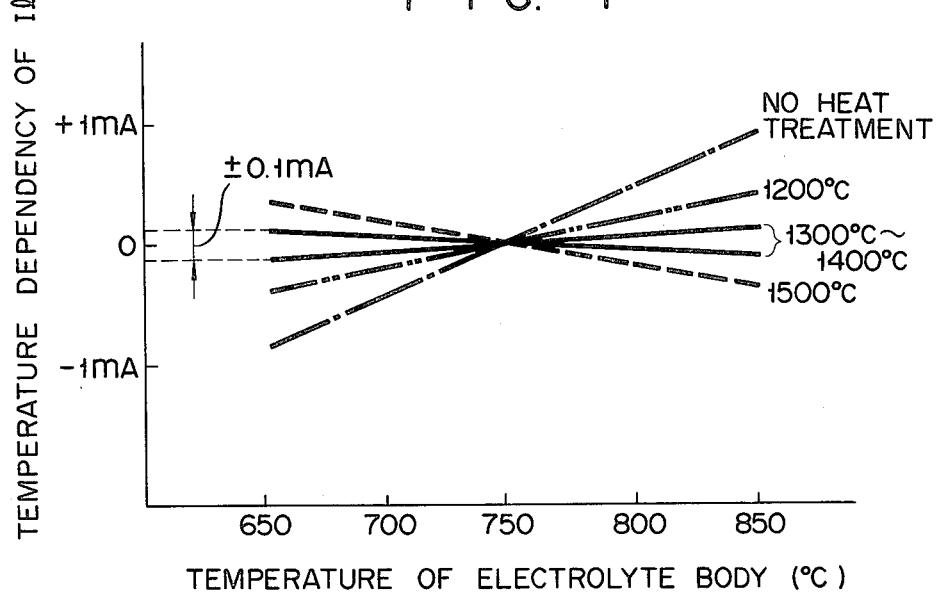
FIG. 4 is a curve diagram showing the dependency of the value Il of the saturated current on the temperature of the solid electrolyte body.

FIG. 4 shows that when the gas diffusion-resisting layer 4 is baked at a temperature of 1,300° C. to 1,400° C., the variation of the value II of the saturated current with the temperature of the solid electrolyte body 1 is extremely minimized. Therefore, when the gas diffusion-resisting layer 4 is formed, it is preferred that the SiO₂ content be set at 1 to 4%, and baking be carried out at a temperature of 1,300° C. to 1,400° C.

Detailed description will now be given with reference to FIGS. 5 and 6 of the construction of an actual oxygen concentration-sensing device intended to detect the oxygen concentration in the exhaust of an automobile.

A solid electrolyte body 1 is shaped like a cup open at the top and closed at the bottom. The body 1 is prepared from an oxygen-ion-permeable metal oxide, such as a mixture of 90 to 95 mol % of zirconium oxide ($ZrO_2$) and 5 to 10 mol % of yttrium oxide ($Y_2O_3$), or other mixture, for example, $ZrO_2$-$Yb_2O_3$, $ZrO_2$-$Sc_2O_3$, $ZrO_2$-CaO, $ZrO_2$-$Th_2O_3$, $ZrO_2$-MgO, $ThO_2$-CaO, $CeO_2$-MgO. An annular larger diameter section 5 is formed around the outer peripheral wall of the electrolyte body 1. A larger diameter seat 6 is formed on that part of the inner peripheral wall of the electrolyte body 1 which lies near its open end.

Figure 6:
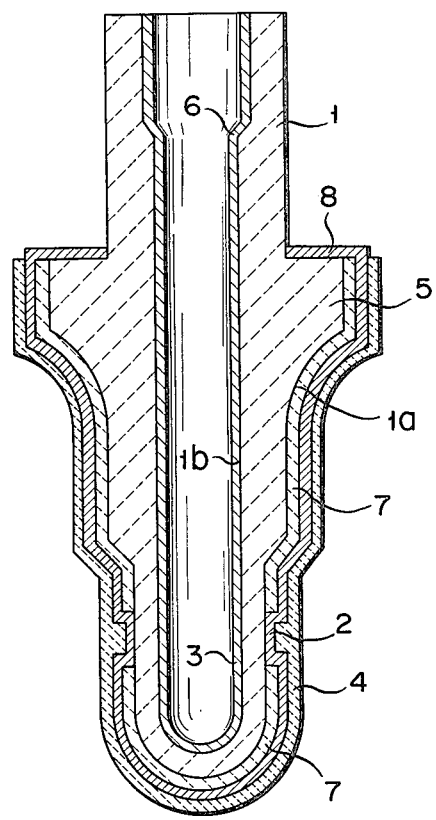
FIG. 6 is an enlarged sectional view of a solid electrolyte body included in FIG. 5.

As indicated in the enlargement in FIG. 6, a first thin porous electrode 2 is tightly fixed to the outer peripheral wall (first surface) 1a of the electrolyte body 1. A second thin porous electrode 3 is also tightly fixed to the inner peripheral wall (second surface) 1b of the electrolyte body 1. That portion of the first electrode 2 which is actually exposed to the exhaust is chosen to have an area of 20 to 100 mm². An electric insulation layer 7 is provided on the outer peripheral wall of the electrolyte body 1 (including the section 5) other than to which the first electrode 2 is fixed. A conductive layer 8 is deposited on the outer peripheral wall of the electric insulation layer 7 in a state electrically connected to the first electrode 2 to function as its lead line, and also extending over the section 5. In this case, it should be noted that the first electrode 2 and conductive layer 8 are integrally formed. Namely, an electric insulation layer 7 is first formed on the outer peripheral wall of the electrolyte body 1 by masking that portion of said body 1 in which the first electrode 2 is to be deposited. Thereafter, the integral first electrode 2 and conductive layer 8 are simultaneously formed over the electric insulation layer 7 and the outer peripheral wall of the electrolyte body 1 including that portion from which the aforesaid mask is taken. The gas diffusion-resisting layer 4 is deposited over the conductive layer 8 and first electrode 2. In this case, the gas diffusion-resisting layer 4 is chosen to have an average pore-size ranging between 300 Å and 400 Å as previously mentioned.

Figure 5:
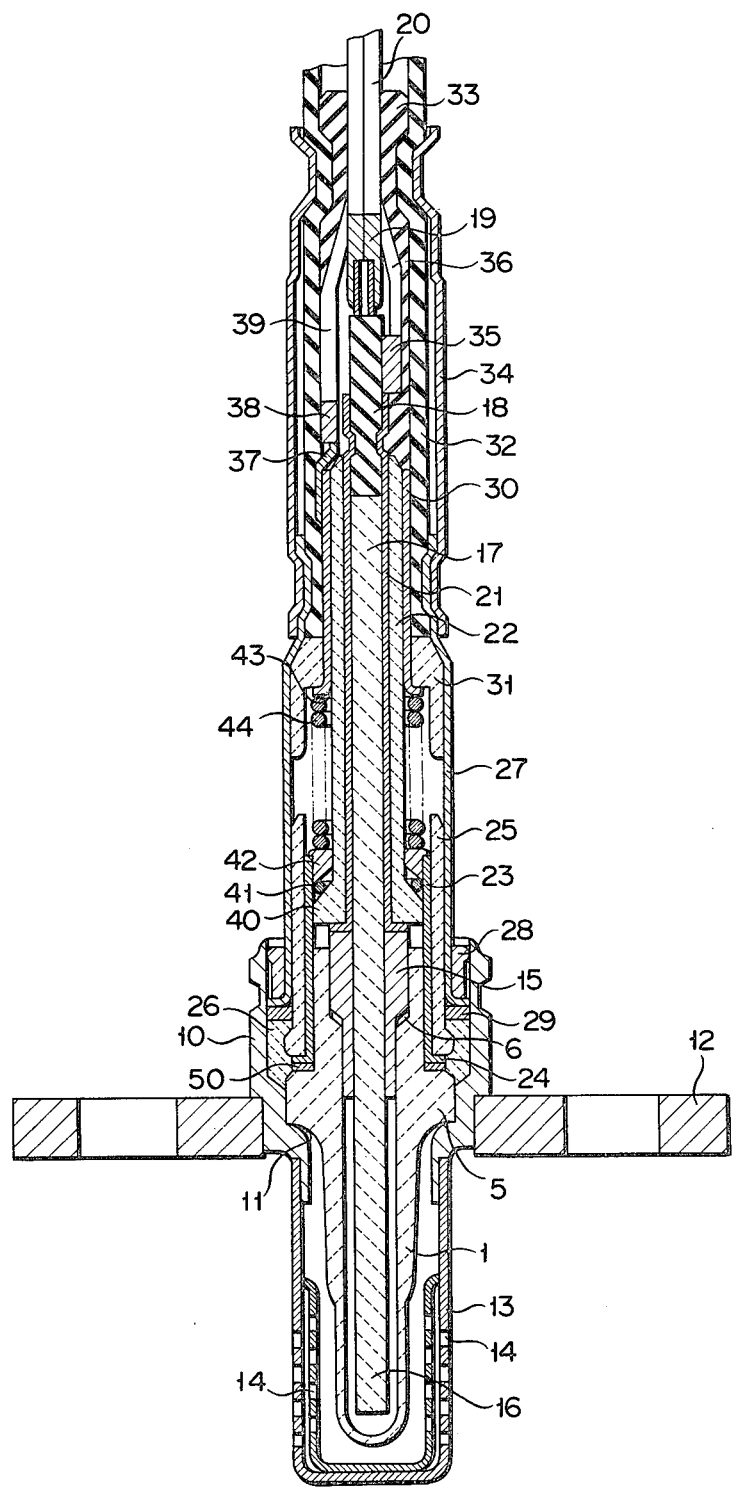
FIG. 5 is a longitudinal sectional view of an oxygen gas concentration-sensing device embodying this invention.

Reverting to FIG. 5, the solid electrolyte body 1 is supported by a holder 10. This holder 10 is shaped like a cylinder whose inner peripheral wall comprises a smaller diameter section 11. The solid electrolyte body 1 is securely fitted into the holder 10 with the annular larger diameter section 5 engaged with the smaller diameter section 11. The holder 10 is provided with a fitting flange 12, which is prepared from SUS 304 stainless steel (JIS). The holder 10 is also prepared from SUS 430 stainless steel (JIS). It will be noted that all stainless steel materials bearing the character "SUS . . . ." are those which are specified in JIS.

Referring to FIG. 5, the lower end of the holder 10 is fitted with a cup-shaped cover 13 enclosing the electrolyte body 1. The cover 13 is prepared from SUS 310 stainless steel. The lower end portion of the cup-shaped cover 13 is formed of spaced double walls, which are provided with a plurality of holes 14 allowing for the passage of the exhaust from the internal combustion engine of an automobile. As seen from FIG. 5, the holes 14 formed in the outer wall of the cup-shaped cover 13 are not made to face those formed in the inner wall of said cover 13.

A metal pipe 15 is fitted into the upper interior region of the electrolyte body 1. The larger diameter section of the metal pipe 15 is engaged with the smaller diameter section 6 of the electrolyte body 1 by means of a ring packing prepared from, for example, copper ring and compression-molded graphite ring (neither shown), thereby assuring the proper location of said metal pipe 15. A rod-shaped ceramic heater 16 is fitted into the pipe 15. The pipe 15 and ceramic heater 16 are fixed together by silver brazing. The ceramic heater 16 extends through the pipe 15 to the bottom of the electrolyte body 1. The ceramic heater 16 is constructed by inserting a coil-shaped Nichrome wire or comb-shaped heating wire into a rod-shaped alumina porcelain. The ceramic heater 16 is applied to quickly heat the electrolyte body 1 to its operation temperature of about 750° C.

The upper end of the ceramic heater 16 is fitted with a coaxially set heat insulating rod 17 made of, for example, alumina ($Al_2O_3$). The upper end of the heat insulating rod 17 is fitted with a coaxially set electric insulation rod 18 prepared from, for example, Teflon. The heating wire (not shown) of the ceramic heater 16 is electrically connected to one end of a lead (not shown) penetrating the heat-insulating rod 17 and electric insulation rod 18. The other end of the lead is electrically connected to a lead 20 through a connector 19 fitted to the upper end of the electric insulation rod 18. The lead 20 is coated with a Teflon layer, and electrically connected to an external power source (not shown).

The upper end of the ceramic heater 16, the heat insulation rod 17 and the lower half of the electric insulation rod 18 are received in a pipe 21 prepared from SUS 304 stainless steel. A flange is integrally formed with the lower end of the pipe 21 in a state pressed against the upper edge of the pipe 15. The pipe 21 is securely caulked to the electric insulation rod 18. The pipe 21 is received in a pipe-shaped electric insulator 22 prepared from $Al_2O_3$. A larger diameter section is formed at the lower end of the electric insulator 22 in a state pressed against the upper plane of the flange.

The upper end of the electrolyte body 1 positioned above its larger annular diameter section 5 is fitted into a pipe 23 prepared from SUS 304 stainless steel. A flange 24 is formed at the lower end of the pipe 23. The flange 24 is pressed against the upper edge of the annular larger diameter section 5 with a ring packing 50 of, for example, nickle interposed therebetween. The pipe 23 is fitted into a pipe-shaped electric insulator 25 prepared from $Al_2O_3$. The lower end of the electric insulator 25 is supported by a holder 10 with a ring-shaped talc porcelain 26 interposed therebetween. The electric insulator 25 is enclosed in a cylindrical protective cover 27 prepared from SUS 304 stainless steel. A flange provided at the lower end of the protective cover 27 is suppported by the holder 10 with insertion therebetween of a ring spacer 28 prepared from SUS 430 stainless steel and a ring pad 29 prepared from ordinary stainless steel. As shown in FIG. 5, the protective cover 27 extends upward to the proximity of the upper end of the heat insulation rod 17.

The upper half of the electric insulator 22 is fitted into a pipe 30 prepared from SUS 304 stainless steel. A flange is formed at the lower end of the pipe 30. A pipe shaped electric insulator 31 prepared from $Al_2O_3$ is interposed between the lower end of the pipe 30 and the protective cover 27 in a state engaged with the flange of the pipe 30. That portion of the outer peripheral wall of the pipe 30 which lies above the electric insulator 31 is covered with a tube prepared from silicone rubber. This silicone rubber tube 32 extends above the connector 19. A silicon rubber bush 33 is fitted into the silicone rubber tube 32. The lower end of the silicone rubber tube 32 is enclosed in a cylindrical dust cover 34 prepared from carbon steel. The lower end of the dust cover 34 is securely caulked on the upper end of the protective cover 27, and the upper end of the dust cover 34 is securely caulked on the silicon rubber tube 32.

A connector 35 is electrically connected to the upper end of the pipe 21, and also to a lead 36 covered with Teflon. The lead 36 is drawn outside of the subject oxygen gas concentration-sensing device. A connector 38 is electrically connected to the upper end of the pipe 30 with a connecting metal part 37 interposed therebetween. The connector 38 is electrically connected to a lead 39 which is also drawn outside of the subject oxygen gas concentration-sensing device.

A ring 41 prepared from copper is pressed against the inclined upper plane 40 of the larger diameter section of the electric insulator 22. A connection ring 42 prepared from copper is pressed against the upper edge of the ring 41. A compression coil spring 44 prepared from SUS 631 stainless copper is inserted between the connection ring 42 and the underside 43 of the flange of the pipe 30 in a state surrounding the electric insulator 22. The compression coil spring 44 urges the pipe 30 and electric insulator 22 in the opposite directions.

The above-mentioned arrangement causes the first electrode 2 to be electrically connected to an external power source and an electric circuit system including a current-measuring circuit through the conductive layer 8, ring packing 50, pipe 23, ring 41, connection ring 42, coil spring 44, pipe 30, connection metal part 37, connector 38 and lead 39. The second electrode 3 is electrically connected to the above-mentioned electric circuit system through the pipes 15, 21, connector 35 and lead 36.

An oxygen concentration-sensing device shown in FIGS. 5 and 6 has the same function as that of FIG. 2, description thereof being omitted. It will be noted that this invention is not limited by the foregoing embodiments. For instance, the solid electrolyte body need not be shaped like a cup, but may have a plate or cylindrical form. Further, the present invention is applicable not only to the measuring of automobile exhaust but also to the air control of, for example, a blast furnace.

What is claimed is:

1. An oxygen gas concentration-sensing device which comprises:
    a solid electrolyte body which is prepared from an oxygen ion-permeable metal oxide and whose first surface is exposed to a gas to be sensed and whose second surface is exposed to a reference gas;
    a first porous electrode fixed to the first surface of the solid electrolyte body;
    a second porous electrode fixed to the second surface of the solid electrolyte body;
    a gas diffusion-resisting layer which is prepared from a porous metal oxide to cover the first electrode and has an average pore-size ranging between 300 Å and 400 Å; and
    means for impressing prescribed voltage across the first and second electrodes.

2. The device according to claim 1, wherein the gas diffusion-resisting layer is chosen to have a thickness ranging between 200 and 500 microns.

3. The device according to claim 2, wherein the solid electrolyte body is prepared from a mixture of 90 to 95 mol % of $ZrO_2$ and 5 to 10 mol % of $Y_2O_3$.

4. The device according to claim 1, wherein the solid electrolyte body is mode of one compound selected from the group consisting of $ZrO_2$-$Yb_2O_3$, $ZrO_2$-$Sc_2O_3$, $ZrO_2$-CaO, $ZrO_2$-$Th_2O_3$, $ZrO_2$-MgO, $ThO_2$-CaO and $CeO_2$-MgO.

5. The device according to claim 1, wherein that part of the surface of the first electrode which is exposed to a gas to be sensed is chosen to have an area ranging between 20 and 100 $mm^2$.

6. The device according to claim 1, wherein an electric insulation layer is deposited on the first surface of the solid electrolyte body other than to which the first electrode is fixed.

7. The device according to claim 6, wherein a conductive layer acting as a lead is deposited on the outer plane of the electric insulation layer in a state electrically connected to the first electrode.

8. The device according to claim 7, wherein the conductive layer and first electrode are integrally formed.

9. The device according to claim 7, wherein the gas diffusion-resisting layer covers not only the first electrode but also the conductive layer.

10. The device according to claim 1, wherein the solid electrolyte body is shaped like a blind test tube, and the first surface of said body denoted its outer peripheral wall and the second surface of said body represents its inner peripheral wall.

11. The device according to claim 10, wherein the outer peripheral wall of the solid electrolyte body is enclosed in a cup-shaped cover provided with a plurality of orifices allowing for the passage of a gas to be sensed.

12. The device according to claim 11, wherein the cover consists of spatially arranged double walls, which are provided with the orifices positioned so as to be prevented from facing each other.

13. The device according to claim 10, wherein the solid electrolyte body shaped like a blind test tube contains a rod-like heating element.

14. A method of forming a gas diffusion-resisting layer for an oxygen gas concentration-sensing device of the type including a solid electrolyte body which is prepared from an oxygen ion-permeable metal oxide and whose first surface is exposed to a gas to be sensed and whose second surface is exposed to a reference gas, a first porous electrode fixed to the first surface of the solid electrolyte body and a second porous electrode fixed to the second surface of the solid electrolyte body which method comprises plasma spraying a mixture of $Al_2O_3$ powder and 1–4% by weight of $SiO_2$ powder on the electrode on the first surface of the solid electrolyte body to produce a porous gas diffusion-resisting layer and heating the gas diffusion-resisting layer to a temperature ranging between 1,300° C. and 1,400° C., thereby reducing the average pore-size to a level ranging between 300° Å and 400° Å.

* * * * *